(12) United States Patent
Chignon

(10) Patent No.: US 6,537,238 B1
(45) Date of Patent: Mar. 25, 2003

(54) ORTHOTIC DEVICE FOR A LOWER LIMB

(76) Inventor: Jean-Jacques Chignon, 33600 Pessae, Roger Chaumet (FR)

( * ) Notice: Subject to any disclaimer, the term of this patent is extended or adjusted under 35 U.S.C. 154(b) by 0 days.

(21) Appl. No.: 09/720,341
(22) PCT Filed: Jun. 15, 1999
(86) PCT No.: PCT/FR99/01412
§ 371 (c)(1), (2), (4) Date: Feb. 8, 2001
(87) PCT Pub. No.: WO99/66868
PCT Pub. Date: Dec. 29, 1999

(30) Foreign Application Priority Data

Jun. 22, 1998 (FR) .......................................... 98/07820

(51) Int. Cl.[7] .................................................. A61F 5/00
(52) U.S. Cl. .......................................... 602/23; 602/27
(58) Field of Search ............................... 602/23, 26–29, 602/5, 16, 65; 128/882; 623/38–39, 47

(56) References Cited

U.S. PATENT DOCUMENTS

| 4,938,777 A | * | 7/1990 | Mason et al. | 602/27 |
| 5,014,690 A | * | 5/1991 | Hepburn et al. | 602/16 |
| 5,022,390 A | * | 6/1991 | Whiteside | 602/23 |
| 5,697,893 A | * | 12/1997 | Rhenter | 602/16 |
| 5,897,514 A | * | 4/1999 | Currier | 602/16 |

FOREIGN PATENT DOCUMENTS

GB 2168610 A * 6/1986 ............. A61F/5/01

* cited by examiner

Primary Examiner—Michael A. Brown
Assistant Examiner—Quang D. Thanh
(74) Attorney, Agent, or Firm—Armstrong, Westerman & Hattori, LLP

(57) ABSTRACT

An orthotic device for a lower limb, comprising a one-foot support, a vertical rod, a cuff for fixing the orthotic device on the calf, the one-foot support being linked to one end of the vertical rod and the cuff being linked to the vertical rod opposite end. The orthotic device is such that the one-foot support is connected to the vertical rod end via a flexible cylindrical sleeve enabling the one-foot support to rotate horizontally with respect to the vertical rod and to rotate vertically with respect to the vertical rod and it comprises a cylindrical ring urged to be interlocked on the elastic sleeve to block the one-foot support vertical rotation relative to the vertical rod without blocking the one-foot support horizontal rotation relative to the vertical rod. The invention is applicable to an orthotic device enabling the user to walk while providing complete freedom to the foot.

13 Claims, 1 Drawing Sheet

ORTHOTIC DEVICE FOR A LOWER LIMB

The present invention concerns an orthosis of the lower limb, and more particularly an orthosis enabling walking and furthermore enabling total freedom of the foot.

BACKGROUND OF THE INVENTION

Rigid ortheses of the lower limb which maintain the knee permanently in the same position of extension are already known. In such cases, walking and standing are possible, but sitting is possible only after removal of the orthosis.

Ortheses hinged at the level of the knee are also known. They are fitted with a lock enabling the knee to be blocked in the extension position to enable walking or standing with a stiff leg. Sitting is possible without removing the orthosis on the leg by release of the lock.

Other ortheses exist with a thigh piece and a legging hinged together at the level of the knee. They are fitted with elastic return devices enabling the leg to be brought back to the extension position. These elastic return devices enable the wearer to have a gait that is more flexible that in the case of rigid ortheses, but as the elastic devices are arranged in the direction of extension, sitting is possible only when the wearer removes or releases them.

The document FR-A-2 599 246 describes an orhtosis hinged at the level of the knee which enables the wearer to stand and walk without any manipulation, given that the knee is assisted elastically both in extension and in flexion.

French patent application FR 94 07 694 describes an orthosis of the lower limb comprising a thigh piece and a legging hinged together at the level of the knee, the articulation on the thigh piece being formed by a hinged assembly including at least one pair of rods arranged laterally with respect to the knee on at least one side. The pair of rods includes a front rod and a rear rod which are each hinged, on the one hand, on the thigh piece, and on the other hand, on the legging, the intersections of the lines corresponding to each pair of rods defining an instantaneous axis of rotation. A tensor is arranged laterally on at least one side between an anchoring point integral with the thigh piece and an anchoring point integral with the legging.

SUMMARY OF THE INVENTION

The known devices, at the level of the junction of the foot with the leg, are either rigid or flexible. When they are rigid, they enable walking, by their rigidity, but do not provide flexibility of the unipodal support to enable, for example, the driving of a car. When they are flexible, for example when they include elastic levators such as a piano wire, a compression spring, or rubber added to a trunnion-mounted device, they fail to offer sufficient rigidity to ensure safe walking as there is no stabilizing effect on the knee. Moreover, the known devices do not enable any rotation of the unipodal support around the vertical axis. The aim of the present invention is, therefore, to overcome these disadvantages.

An initial aim of the present invention is to provide an orthosis capable of going from a rigid state to a flexible state, in order to enable, alternately, safe walking and freedom of the unipodal support in rotation around to the vertical axis, and control of rotations in walking. Another aim of the invention is to provide an orthosis capable of going from the rigid state to the flexible state simply and practically.

The invention thus concerns an orthosis comprised of a unipodal support, a vertical rod which may be rigid, a cuff enabling the fixing of the orthosis to the calf, the unipodal support being connected to one end of the vertical rod and the cuff being connected to the opposite end of the vertical rod. The orthosis is such that the unipodal support is connected to one end of the vertical rod by means of a flexible cylindrical sleeve enabling the horizontal rotation of the unipodal support around the vertical rod, i.e., rotation around a main longitudinal axis of the vertical rod, and the vertical rotation of the unipodal support around the vertical rod, i.e., rotation around an axis perpendicular to the main longitudinal axis of the vertical rod, and that it includes a cylindrical bushing force-fitted on to the elastic sleeve so as to block in at least one direction the vertical rotation of the unipodal support around the vertical rod without blocking the horizontal rotation of the unipodal support around to the vertical rod.

According to one characteristic of the invention, the sleeve is a core-less cylinder in flexible material including a fastening at each end, these fastenings being independent of each other.

According to another characteristic of the invention, the sleeve includes a rigid base in which the bushing meshes. Advantageously, the sleeve and the bushing have corresponding diameters. Preferably, the bushing has an inside diameter equal to the outside diameter of the rigid base, to within the necessary tolerances, so that the bushing meshes with the base. Provision can be made for the longitudinal axis of the unipodal support to form an angle with the axis of symmetry of the cuff so that the vertical axis is situated laterally outwards in relation to the wearer.

According to yet another characteristic of the invention, the vertical rod may consist of a flexible foil, hollowed in the center, to enable the fitting of a reinforcement so as to increase or decrease the rigidity of the rod when the bushing is in position in the base, and the sleeve may be made of natural or synthetic rubber.

According to one mode of implementation, the bushing is raised to enable a vertical rotation movement of the unipodal support around to the vertical rod.

DESCRIPTION OF EMBODIMENTS

Figure 1:
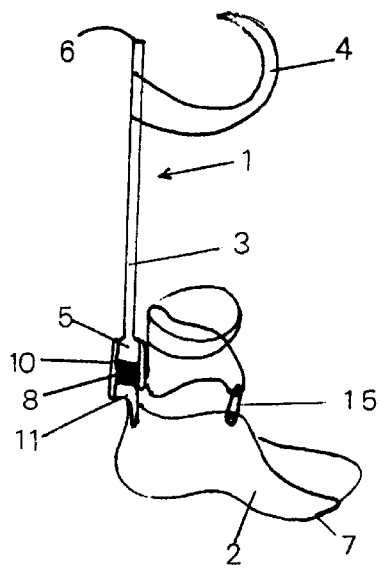
FIG. 1 is a side view of an example of orthosis according to the present invention.

In the example of orthosis represented in the figures, the flexible foil 12 is hollowed in its center to enable the positioning of a reinforcement 13 to increase or decrease the rigidity of the rod 3 when the bushing 10 is in position in the base. Thus, the rod 3 is hollowed in its center to enable the fitting of reinforcement 13. The cuff 4 is connected to the upper end 6 of the vertical rod. The cuff 4 may include a fastening system not shown, such as a system by a Velcro® strip. The unipodal support 2 includes a base 7 designed to rest on the ground. This base may be hollow and in rigid plastic. The unipodal support 2 is connected to the end 5 of the vertical rod 3 and the cuff 4 is connected to the opposite end 6 of the vertical rod 3.

Figure 2:
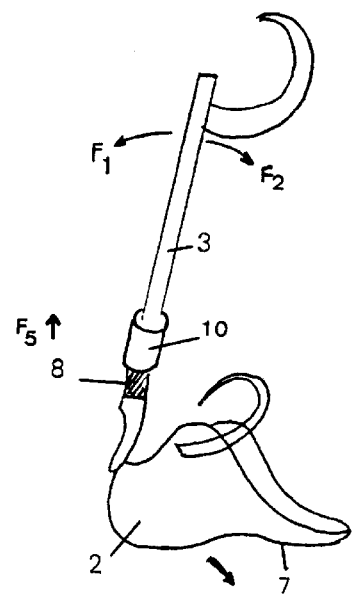
FIG. 2 is a side view of the orthosis of FIG. 1 with a raised bushing.

According to the invention, the unipodal support 2 is connected to the lower end 5 of the vertical rod 3 by means of a cylindrical sleeve 8. This sleeve 8 is flexible and enables the horizontal rotation of the unipodal support around the vertical axis defined by vertical rod 3. Furthermore, the flexible sleeve 8 enables vertical rotation of the unipodal support 2 with respect to vertical rod 3. As can be seen in FIG. 2, when the base 7 of the unipodal support 2 rests on the ground, the vertical rod is mobile in the vertical plane according to the arrows F1 and F2.

Figure 5:
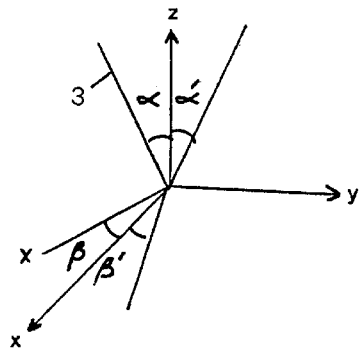
FIG. 5 is an illustrative representation of rotational directions.
Figure 4:
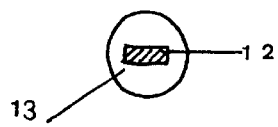
FIG. 4 is a cross-sectional view of a vertical rod of the orthosis of FIG. 1.

FIG. 5 illustrate the horizontal plane xy representing the horizontal ground and the z axis representing the vertical. When the base 7 of the unipodal support 2 is in the xy plane, the vertical rod 3 of the device can move between the vertical and an angle α inclined in relation to the vertical or an angle α' in the opposite direction. In the present invention, this is called the vertical rotation of the unipodal support 2 in relation to the vertical rod 3.

Figure 3:
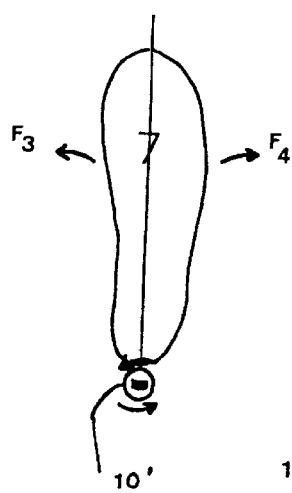
FIG. 3 is a schematic top view of the orthosis of FIG. 1 showing rotational movements.

According to the invention, when its base 7 is resting on the ground, namely in the plane xy, the unipodal support 2 is mobile in a horizontal plane in relation to the vertical rod 3 according to the arrows F3 and F4, as shown in FIG. 3. As can be seen in FIG. 5, the longitudinal axis of the unipodal support 2 is mobile around the z axis according to an angle β and according to an angle β' in the opposite direction.

Consequently, according to the invention, the orthosis enable a rotational movement of the unipodal support horizontally by torsion of the sleeve, and vertically downwards.

According to the present invention, the orthosis is such that it includes a cylindrical bushing 10 which can take two different positions. The first position, illustrated in FIG. 1, is such that the bushing 10 meshes on the sleeve 8 so as to block the vertical rotation of the unipodal support in relation to the vertical axis 3. The second position, illustrated in FIG. 2, is such that the bushing 10 is released from the sleeve 8. The bushing 10 has an inside diameter which corresponds to the outside diameter of the sleeve 8. The sleeve 8 is a core-less rubber cylinder with a fastening at each end. These fastenings are independent of each other. The first, upper fastening 16 connects the sleeve 8 to the rod 3, and the second, lower fastening 17 connects the unipodal support 2 to the sleeve 8. The sleeve includes a rigid base 11 into which the bushing 10 meshes. When the bushing 10 is blocked in the meshed position on the base 11 of the sleeve 8, vertical rotation of the vertical rod 3 and of the unipodal support 2 in relation to each other is impossible. On the other hand, in this position, the unipodal support 2 can rotate horizontally around the vertical rod 3. When the bushing 10 is raised in the direction of the arrow F5, as shown in FIG. 3, the sleeve 8 is freed, such that the bushing 10 rests on the sleeve 8. Vertical rotation of the unipodal support 2 is then possible.

Figure 6:
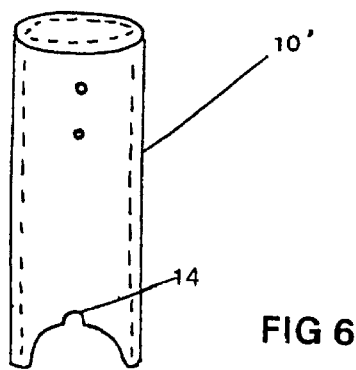
FIG. 6 is a side view of a bushing of the orthosis of FIG. 1 in an alternative embodiment.

The force fitting-of the bushing 10 on the sleeve 8 is performed thanks to the base 11 of the sleeve 8, said base 11 having an outside diameter equal to the inside diameter of the bushing 10. Thus, in the position illustrated in FIG. 1, rigid holding is obtained according to the vertical axis and the unipodal support cannot move forward or backwards. This position enables walking, while at the same time enabling rotations. In this position, such as illustrated more particularly in FIG. 3, the unipodal support 2 can rotate in relation to the vertical rod thanks to the elastic sleeve 8, enabling an active control of the rotations by torsion of the sleeve. In the second position, illustrated in FIG. 2, the bushing being raised, the flexible sleeve enables upward movements of the unipodal support 2. The orthosis then becomes flexible and enables, for example, the driving of a car. The device according to the present invention therefore enables both walking with a rigid orthosis matching physiological requirements, and is changed into a flexible orthosis for other activities that do no require vertical rigidity. FIG. 6 illustrates a bushing 10' made according to a variation and slightly modified in comparison with the bushing 10 described above, to provide the user with a greater freedom of choice in the movements enabled or not enabled by the orthosis made according to the present invention.

According to this variation, the bushing 10' is cylindrical. The upper end (in the position of use) of this bushing 10' is circular and corresponds to a cross section of the cylinder according to a plane perpendicular to the axis of the cylinder. The lower end (in the position of use) of this busing 10' is generally of an oval shape, corresponding to a cross-section of the cylinder according to a plane or curved surface (as illustrated in FIG. 6), generally not perpendicular to the axis of the cylinder. As a result, the bushing 10' presents a part with a maximal axial length (measured according to the axis of the cylinder) greater than the minimal axial length of a part diametrically opposite (in relation to the axis of the cylinder). Moreover, an opening 14 may be made in the bushing 10' for example in the part of the bushing 10' with a minimal length.

The orthosis, in compliance in all other respects with the description above, may be fitted with a bushing 10' instead of the bushing 10. In such conditions, the bushing 10' provides additional choice in the degrees of freedom possible in vertical rotation of the unipodal support of the orthosis. Depending on the orientation given to the part with the greater axial length, namely forwards or backwards (in relation to the patient), vertical rotation of the unipodal support forwards or backwards respectively will not be possible, whilst rotation in the other direction will be possible.

So as to keep the orientation of the bushing 10' in relation to the unipodal support, means of locking or adjusting the rotation of the bushing 10' in relation to the sleeve 8 can be provided, for example by providing a notch 14 in the bushing 10'. This notch 14 is designed to take a screw (not shown) corresponding to a tapped hole made in the base 11. This makes it possible to prevent or limit any possibility of movement, either forwards or backwards, whilst maintaining the possibility of rotational movements to the right or to the left.

Whenever the patient so wishes, or is enabled to do so, he has the possibility of performing movement forwards or backwards by setting the bushing 10'. The movement will be possible on the side where the axial length is shortest, without rasing the bushing 10'. Return means such as elastics 15 provide assistance to the movement thus enabled.

What is claimed is:

1. An orthosis comprising a unipodal support, a vertical rod, a cuff enabling the fastening of the orthosis to a wearer's calf, the unipodal support being connected to one end of the vertical rod and the cuff being connected to an opposite end of the vertical rod, wherein the unipodal support is connected to the end of the vertical rod by means of a flexible cylindrical sleeve enabling (i) rotation of the unipodal support around a longitudinal axis of the vertical rod and (ii) rotation of the unipodal support around an axis perpendicular to the vertical rod, and a cylindrical bushing is provided on the vertical rod, said cylindrical bushing meshing on the flexible sleeve so as to block in at least one direction the rotation of the unipodal support around the axis perpendicular to the vertical rod without blocking the rotation of the unipodal support around the longitudinal axis of the vertical rod.

2. The orthosis according to claim 1, wherein the sleeve is a core-less cylinder in flexible material including a fastening at each of its ends, said fastenings being independent of each other.

3. The orthosis according to claim 2, wherein the sleeve includes a rigid base in which the bushing meshes.

4. The orthosis according to claim 3, wherein the sleeve and the bushing have equal diameters.

5. The orthosis according to claim 3, wherein the bushing has an inside diameter approximately equal to an outside diameter of the rigid base, with necessary tolerances such that the bushing meshes in the rigid base.

6. The orthosis according to claim 1, wherein, such that the longitudinal axis of the vertical rod is situated laterally on the outside with respect to the wearer.

7. The orthosis according to claim 2, wherein the vertical rod is a flexible foil, hollowed in a center portion thereof, so as to enable the positioning of a reinforcement to increase or decrease the rigidity of the rod when the bushing is in position on the base.

8. The orthosis according to claim 1, wherein the sleeve is in natural or synthetic rubber.

9. The orthosis according to claim 1, wherein the bushing is movable in an upward direction so as to reach a position which enables the rotation of the unipodal support around the axis perpendicular to the vertical rod.

10. The orthosis according to claim 1, wherein the bushing is movable between a high position and a low position and includes a part with an axial length smaller than that of a part diametrically opposite, so that, when the bushing is maintained in the low position, rotation of the unipodal support around the axis perpendicular to the vertical rod in a direction toward the part with the smaller axial length is enabled, while rotation of the unipodal support around the axis perpendicular to the vertical rod in a direction toward the part diametrically opposite is prevented.

11. The orthosis according to claim 10, comprising return devices to provide assistance for moving the unipodal support.

12. The orthosis according to claim 11, wherein the return devices are elastic bands.

13. The orthosis according to claim 1, wherein the vertical rod is rigid.

* * * * *